United States Patent [19]

Reimschuessel et al.

[11] Patent Number: 4,594,452

[45] Date of Patent: Jun. 10, 1986

[54] PROCESS FOR THE PREPARATION OF ANHYDROUS N-(3-CHLORO-2-HYDROXYPROPYL) TRIALKYLAMMONIUM SALTS

[75] Inventors: Herbert K. Reimschuessel, Morristown; Michael A. Kocur, Union, both of N.J.

[73] Assignee: Allied Corporation, Morris Township, N.J.

[21] Appl. No.: 748,083

[22] Filed: Jun. 24, 1985

[51] Int. Cl.$^4$ ............................................. C07C 91/26
[52] U.S. Cl. ................................................... 564/292
[58] Field of Search ......................................... 564/292

[56] References Cited

U.S. PATENT DOCUMENTS 2,876,217  3/1959  Paschall et al. .................. 260/233.3
3,532,751 10/1970  Langher et al. .................. 260/567.6
3,558,501  1/1971  McGuire et al. .................... 252/182

OTHER PUBLICATIONS

Mehltretter, et al. "Effect of Temperature and Concentration on the Chlorohydrination of Allyltrimethylammonium Chloride," I & E Product Research & Development, vol. 8, pp. 279–281, (1969).

Primary Examiner—Paul R. Michl
Assistant Examiner—Alex H. Walker
Attorney, Agent, or Firm—Arthur J. Plantamura; Jay P. Friedenson

[57] ABSTRACT

The preparation of anhydrous, pure, crystalline N-(3-chloro-2-hydroxypropyl) trialkylammonium salts is disclosed by a process entailing reaction of epichlorohydrin with a trimethylammonium salt in an organic solvent which is a solvent for the two reactants and a non-solvent for the reaction product.

A fine crystalline, chemically pure, anhydrous N-(3-chloro-2-hydroxypropyl) trimethylamine hydrochloride is produced by a process that does not entail an aqueous medium or the use of gaseous trimethylamine. The process comprises reacting trimethylammonium chloride with epichlorohydrin in an organic solvent which is a solvent for either of the two reactants and a non-solvent for the reaction product. Though a number of organic solvents may be used, it was found that chloroform was particularly suited. The reaction proceeds readily at temperatures within the range of 0° to 50° C. and results, depending on the reaction conditions, in 80% to 97% yields of pure N-(3-chloro-2-hydroxypropyl) trimethylammonium chloride with respect to the trimethylamine hydrochloride. The trimethylamine hydrochloride is the preferred starting material, however, the process may be applied to other trialkylamine hydrochlorides such as those containing alkyl groups with 2 to 12 carbon atoms, or those containing different alkyl groups. Furthermore, the process may also be applied to other trialkylammonium salts, such as other halides, nitrates, sulfates and perchlorates.

6 Claims, No Drawings

PROCESS FOR THE PREPARATION OF ANHYDROUS N-(3-CHLORO-2-HYDROXYPROPYL) TRIALKYLAMMONIUM SALTS

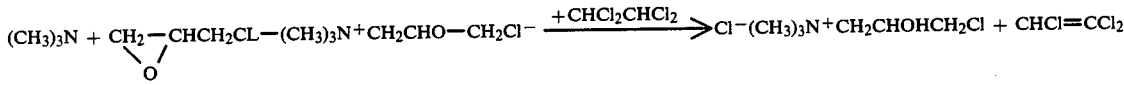

DESCRIPTION

This invention relates to the preparation of anhydrous, pure, crystalline N-(3-chloro-2-hydroxypropyl)-trialkyl ammonium salts and more particularly to the preparation of said salts by a process entailing reaction of epichlorohydrin with a trimethylammonium salt in an organic solvent which is a solvent for the two reactants and a non-solvent for the reaction product.

BACKGROUND OF THE INVENTION

Members of the class of anhydrous N-(3-chloro-2-hydroxypropyl)trialkyl ammonium salts, such as the N-(3-chloro-2-hydroxypropyl)trimethyl ammonium chloride (CHPTMAC), are reactive chemical intermediates and are used in industrial operations for the modification of both natural and synthetic polymers. Particularly, extensive is their use for the production of cationic polysaccharides entailing reaction with starch and cellulose.

It is known that CHPTMAC can be obtained by reaction of epichlorohydrin with trimethylamine hydrochloride. According to U.S. Pat. No. 2,876,217, this reaction is conducted in an aqueous system and the CHPTMAC reaction product is obtained in the form of an aqueous solution. A disadvantageous consequence of conducting the reaction in an aqueous medium, according to U.S. Pat. No. 2,876,217, is the occurrence of a series of side reactions which, for instance, result in the formation of structures such as 1,3-bis(trimethylammonium)-2-hydroxypropane dichloride, which if not removed will contaminate any subsequent reaction product. A further potential and very undesirable by-product of this process is the 1,3-dichloropropanol-2 which may cause crosslinking in subsequent reactions.

Formation of undesirable by-products characterizes also a known process which entails hypochlorination of allyl quaternary ammonium salts. This process is also conducted in an aqueous medium and may be carried out according to the disclosures found in U.S. Pat. Nos. 3,532,751 and 3,558,501. In addition to the by-products mentioned above, this process results in a mixture of N-(2-chloro-3-hydroxypropyl)- and N-(3-chloro-2-hydroxypropyl)trimethylammonium chlorides, and appreciable quantities of the chlorination product N(2,3-dichloropropyl)trimethylammonium chloride (I&EC Product Res. & Dev. 8,279 (1969)). Therefore, the known approaches of the prior art result in aqueous solutions that, in most cases, require careful purification, such as described by Paschell in U.S. Pat. No. 2,876,217 prior to further use. It has, therefore, been proposed that the N-(3-chloro-2-hydroxypropyl)trimethylammonium chloride be prepared in an anhydrous crystalline form. According to European Pat. No. 0,005,223, this product is obtained by a process that entails use and reaction of both gaseous trimethylamine and tetrachloroethane. Disadvantages of this process are the need to operate with gaseous trimethylamine and the formation of the by-product trichloroethylene according to the reaction:

According to European Patent Application No. 0,055,796, the undesirable use of the toxic trimethylamine for the production of a solid product is circumvented by use of an aqueous trimethylamine hydrochloride solution for the reaction with epichlorohydrin, and subsequent removal of water by azeotropic distillation. Since however, in this process the principal reaction is conducted in an aqueous medium, this approach also is characterized by all the disadvantageous consequences arising from the operation in an aqueous system as discussed earlier. Furthermore, the additional process steps necessitated by the azeotropic distillation affect unfavorably the economics of the process, particularly when a truly anhydrous crystalline product is desired.

It is, accordingly, apparent that a need exists for an improved method for the preparation of anhydrous, pure, crystalline N-(3-chloro-2-hydroxypropyl)trimethylammonium chloride wherein the product can be produced conveniently by a simple process that does not entail an aqueous medium or the use of gaseous trimethylamine.

SUMMARY OF THE INVENTION

According to the invention, the preparation of anhydrous, pure, crystalline N-(3-chloro-2-hydroxypropyl)-trialkyl ammonium salts is effected by a process entailing reaction of epichlorohydrin with a trialkylammonium salt of the formula:

$$HN^+R^1R^2R^3X^-$$

wherein $R^1$, $R^2$ and $R^3$ are alkyl or hydroxyalkyl groups the number of carbon atoms of each one is either the same or different at each occurrence and is in the range of 1 to 12, and $X^-$ is an anion such as selected from halide, nitrate, sulfate, and perchlorate in an organic solvent which is a solvent for the two reactants and a non-solvent for the reaction product. In a preferred process of the invention, trimethylamine hydrochloride is reacted with epichlorohydrin in an organic solvent which is a solvent for either of the two reactants and a non-solvent for the reaction product. As the organic solvent chloroform is particularly suitable. The reaction proceeds readily at temperatures within the range of 0° to 50° C. and results, depending on the reaction conditions, in 80% to 97% yields of pure N-(3-chloro-2-hydroxypropyl)trimethylammonium chloride with respect to the trimethylamine hydrochloride. Although trimethylamine hydrochloride is the preferred starting material, the process according to this invention may be applied to other trialkylammonium chlorides such as triethylamine hydrochloride, triethanolamine hydrochloride, tripropylamine hydrochloride, trihexylamine hydrochloride, trioctylamine hydrochloride, trinonylamine hydrochloride, triadecylamine hydrochloride, tridodecylamine hydrochloride and the like. Furthermore, the process of the invention may also be applied to other trialkylammonium salts, such as other halides, nitrates, sulfates and perchlorates.

DESCRIPTION OF THE PREFERRED EMBODIMENTS

According to the invention, we have discovered that a fine crystalline, chemically pure, anhydrous N-(3-chloro-2-hydroxypropyl)trimethylammonium salt of the general formula:

$$ClCH_2CHOHCH_2N^+R^1R^2R^3X^-$$

where $R^1$, $R^2$ and $R^3$ are alkyl groups the number of carbon atoms of each one is either the same or different at each occurrence, and is in the range of 1 to 12, and $X^-$ is an anion selected from halide, nitrate, sulfate and perchlorate
can be produced conveniently by a simple process that does not entail an aqueous medium or the use of gaseous trimethylamine. This discovery comprises reacting a salt, typically trimethylamine hydrochloride, with epichlorohydrin in an organic solvent which is a solvent for either of the two reactants and a non-solvent for the reaction product. Salts of the kind contemplated are those of the formula:

$$HN^+R^1R^2R^3X^-$$

wherein $R^1$, $R^2$ and $R^3$ are alkyl or hydroxy alkyl groups the number of carbon atoms of each one is either the same or different at each occurrence, and is in the range of 1 to 12 and $X^-$ is an anion selected from halide, nitrate, sulfate, and perchlorate. Though a number of organic solvents may satisfy this condition, it was found that chloroform was particularly suited. The reaction proceeds readily at temperatures within the range of 0° to 50° C. and results, depending on the reaction conditions, in 80% to 97% yields of pure N-(3-chloro-2-hydroxypropyl)trimethylammonium chloride with respect to the trimethylamine hydrochloride.

Though the trimethylamine hydrochloride is preferred, the invention may be applied to other trialkylamine salts such as those of the formula:

$$HN^+R^1R^2R^3X^-$$

wherein $R^1$, $R^2$ and $R^3$ are alkyl or hydroxy alkyl groups the number of carbon atoms of each one is either the same or different at each occurrence, and is in the range of 1 to 12 and $X^-$ is an anion selected from halide, nitrate, sulfate, and perchlorate. Illustrative of such other chloride salts are triethylamine hydrochloride, triethanol amine hydrochloride, tripropylamine hydrochloride, trihexylamine hydrochloride, trioctylamine hydrochloride, trinonylamine hydrochloride, tridecylamine hydrochloride, tridodecylamine hydrochloride and the like. Furthermore, the process of this invention may also be applied to other trialkylamine salts, such as other halides, nitrates, sulfates and perchlorates. Illustrative of such other exemplary salts are trimethylamine hydrobromide, triethylammonium nitrate, tripropylamine sulfate, trihexylamine nitrate, and trioctylamineperchlorate, and the like.

The following examples are given to illustrate the present invention. It will be understood that although the examples may describe in detail certain preferred operating conditions of the invention, they are given primarily for purposes of illustration and the invention in its broader aspects is not limited thereto. Parts stated are parts by weight unless expressly indicated otherwise.

EXAMPLE 1

To a stirred solution of 95.6 g (1 mole) trimethylamine hydrochloride in 850 ml chloroform was added gradually 95.3 g (1.03 moles) epichlorohydrin. The reaction mixture was held at a temperature of 35° C. and blanketed with nitrogen. After stirring for about 80 minutes, the solution turned cloudy and a crystalline product started to form. After 20 hours, the reaction mixture was cooled to room temperature and the crystalline reaction product was collected on a filter, washed several times with chloroform and subsequently with ether. After drying in a vacuum oven at 25° C. 167.4 g of a dry, fine crystalline product was obtained. Upon heating the crystals compacted at 189° C. and melted between 193° C. to 194° C. to a clear, slightly amber liquid which upon cooling solidified at 192° C.

Both melting point and solidification temperature of the product obtained according to the process of this invention are indicative of a purity exceeding those of products obtained by prior art which were characterized by melting points reported to be in the range of 187° C. to 189° C.

The high purity was also confirmed by C13 NMR analysis in D$_2$O solution. A triplet at 55.11 ppm was due to spin-spin coupling of the methyl carbons with $^{14}$N. A second triplet at 69.20 was due to the $^{14}$N bonded CH$_2$, whereas the CH$_2$Cl group gave rise to a singlet of 47.84 ppm. Finally, the peak for the carbon of the CHOH group appeared at 66.39 ppm. (Dioxane was used as the internal standard. The reference peak appeared at 67.4 ppm). The complete absence of any other peaks in the NMR spectrum indicated that the material was pure.

EXAMPLE 2

This example demonstrates the preparation of an aqueous solution without prior isolation of the crystalline product.

The crystalline reaction product is obtained in a manner similar to the method followed in Example 1 except that at the end of the reaction water is introduced into the reactor to dissolve the crystalline product. This is followed by separation of the organic phase. (The resulting aqueous solution may be used directly for further reaction, or if required, purified by extraction with an additional quantity of the corresponding solvent.) Thus, after 20 hours of reaction as in Example 1, 200 ml of water was added, the mixture was stirred until all of the solids were dissolved, after separation of the two liquid phases, the chloroform phase was removed and the aqueous phase extracted two times, each with 150 ml chloroform. After final separation, an aqueous solution was obtained containing about 45% of CHPTMAC.

It will be understood that variations may be made within the disclosed limitations and accordingly, the invention should not be limited except as set forth in the claims.

What is claimed:

1. A process for the production of pure, anhydrous, crystalline N-(3-chloro-2-hydroxypropyl)trialkylammonium salt of the general formula:

$$ClCH_2CHOHCH_2N^+R^1R^2R^3X^-$$

where $R^1$, $R^2$ and $R^3$ are alkyl groups the number of carbon atoms of each one is either the same or different at each occurrence, and is in the range of 1 to 12, and $X^-$ is an anion selected from halide, nitrate, sulfate, and perchlorate;

which comprises reacting a trialkylamine salt of the formula:

$$HN^+R^1R^2R^3X^-$$

wherein $R^1$, $R^2$ and $R^3$ are alkyl or hydroxy alkyl groups the number of carbon atoms of each one is either the same or different at each occurrence, and is in the range of 1 to 12 and $X^-$ is an anion selected from halide, nitrate, sulfate, and perchlorate which has been dissolved in a suitable organic solvent, with epichlorohydrin at a temperature in the range of from about 0° C. to about 50° C. and separating the solid reaction product from the reaction medium; said organic solvent being selected from the group of organic solvents that dissolve epichlorohydrin and the particular trialkylamine salt, and are non-solvents for the resultant N-(3-chloro-2-hydroxypropyl)trialkylammonium salt.

2. The process of claim 1 wherein the solution comprises trimethylamine hydrochloride-chloroform.

3. The process of claim 1 wherein the salt is trimethylamine hydrochloride.

4. The process of claim 1 wherein the salt is triethylamine hydrochloride.

5. The process of claim 1 wherein the salt is triethanolamine hydrochloride.

6. The process of claim 1 wherein the salt is trimethylammonium nitrate.

* * * * *